United States Patent
Bühren et al.

(10) Patent No.: US 10,123,687 B2
(45) Date of Patent: Nov. 13, 2018

(54) METHOD FOR OPTIMIZING THE SELECTION OF THE IOL TO BE IMPLANTED IN AN EYE

(71) Applicant: Carl Zeiss Meditec AG, Jena (DE)

(72) Inventors: Tobias Bühren, Magdala (DE); Michael Trost, Stadtroda (DE); Christopher Weth, Aalen (DE); Ferid Bajramovic, Jena (DE); Wei-Jun Chen, Jena (DE); Martin Volkwardt, Kröslin (DE); Michael Zimmermann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 189 days.

(21) Appl. No.: 15/103,299

(22) PCT Filed: Dec. 9, 2014

(86) PCT No.: PCT/EP2014/077074
§ 371 (c)(1),
(2) Date: Jun. 9, 2016

(87) PCT Pub. No.: WO2015/086611
PCT Pub. Date: Jun. 18, 2015

(65) Prior Publication Data
US 2016/0302660 A1  Oct. 20, 2016

(30) Foreign Application Priority Data

Dec. 10, 2013 (DE) .................. 10 2013 020 706

(51) Int. Cl.
*A61B 3/00* (2006.01)
*A61B 90/00* (2016.01)
(Continued)

(52) U.S. Cl.
CPC ............ *A61B 3/0025* (2013.01); *A61B 3/102* (2013.01); *A61B 3/1005* (2013.01); *A61B 3/107* (2013.01);
(Continued)

(58) Field of Classification Search
CPC .. A61B 3/102; A61B 3/0025; A61B 2034/102
(Continued)

(56) References Cited

U.S. PATENT DOCUMENTS

| 7,452,077 B2 | 3/2008 | Meyer et al. |
| 2011/0273669 A1 | 11/2011 | Abitbol et al. |
| 2014/0192317 A1* | 7/2014 | Buhren .................... A61B 3/10 351/205 |

FOREIGN PATENT DOCUMENTS

| DE | 602 13 260 T2 | 7/2007 |
| DE | 10 2008 051 272 A1 | 4/2010 |

(Continued)

OTHER PUBLICATIONS

PCT International Search Report for International Application No. PCT/EP2014/077074, dated Feb. 10, 2015, 3 pages.
(Continued)

*Primary Examiner* — Hung Dang
(74) *Attorney, Agent, or Firm* — Patterson Thuente Pedersen, P.A.

(57) ABSTRACT

A method for selecting an intraocular lens (IOL), to optimize the results of refractive procedures on the eye. According to the invention, the method for selecting the IOL includes: a) determining the required biometrical parameters of the eye; b) using the parameters for a corresponding eye model; c) evaluating, using ray tracing, the data of an IOL to be implanted; d) selecting, on the basis of said data, an IOL to be implanted; and e) repeating the method steps c) and d) for further suitable IOLs. To optimize the method, different
(Continued)

measuring methods are used to determine the biometrical parameters, a corresponding patient-specific eye model is identified, and, when selecting the IOL, additional retinal image metrics are taken into consideration alongside the determined data. The method according to the invention permits the optimized selection of a spherical, aspheric, toric or multifocal IOL for implantation.

28 Claims, 1 Drawing Sheet

(51) Int. Cl.
  *A61B 3/10*    (2006.01)
  *A61B 3/107*   (2006.01)
  *A61B 3/11*    (2006.01)
  *A61B 3/117*   (2006.01)
  *A61B 3/12*    (2006.01)

(52) U.S. Cl.
  CPC ............ *A61B 3/112* (2013.01); *A61B 3/1173* (2013.01); *A61B 3/12* (2013.01); *A61B 90/06* (2016.02); *A61B 2090/061* (2016.02)

(58) Field of Classification Search
  USPC .................. 351/205, 206, 246; 623/6.11
  See application file for complete search history.

(56) References Cited

FOREIGN PATENT DOCUMENTS

| | | |
|---|---|---|
| DE | 10 2011 103224 A1 | 12/2012 |
| DE | 10 2011 103233 A1 | 12/2012 |
| DE | 10 2011 113953 A1 | 3/2013 |
| DE | 10 2012 016 379 A1 | 2/2014 |
| DE | 10 2012 019 474.9 | 4/2014 |
| DE | 10 2012 019 473.0 | 6/2014 |
| WO | WO 2010/035139 A2 | 4/2010 |
| WO | WO 2012/062453 A1 | 5/2012 |

OTHER PUBLICATIONS

English translation of PCT International Search Report for International Application No. PCT/EP2014/077074, dated Feb. 10, 2 pages.
DE Search Report for DE 10 2013 020 706.3, dated Sep. 26, 2014, 9 pages.
Partial English translation of DE Search Report for DE 10 2013 020 706.1, dated Sep. 26, 2014, 5 pages.
Preussner, P.-R. et al., "Intraocular lens calculation accuracy limits in normal eyes," J Cataract Refract Surg—vol. 34, May 2008, 7 pages.
Preussner, P.-R. et al., "Ray tracing for intraocular lens calculation," J Cataract Refract Surg—vol. 28, Aug. 2002, 8 pages.
English translation of PCT International Preliminary Report on Patentability for International Application No. PCT/EP2014/077074, dated Jun. 14, 2016, 10 pages.

\* cited by examiner

METHOD FOR OPTIMIZING THE SELECTION OF THE IOL TO BE IMPLANTED IN AN EYE

RELATED APPLICATIONS

This application is a National Phase entry of PCT Application No. PCT/EP2014/077074 filed Dec. 9, 2014, which application claims the benefit of priority to German Application No. 10 2013 020 706.1, filed Dec. 10, 2013, the entire disclosures of which are incorporated herein by reference.

FIELD OF THE INVENTION

The present invention relates to a method for optimizing the selection of the intraocular lens (IOL) to be implanted in an eye, in order to optimize the results of refractive procedures on the eye.

BACKGROUND

A fundamental prerequisite for this is the correct determination of the biometric data of the eye required for the selection of an IOL.

According to the known state of the art, IOLs are selected or adapted on the basis of measured and/or estimated variables, wherein only individual parameters in the form of individual measured values or as an average value for defined patient groups are taken into consideration.

For one thing, the biometric data of the eye to be treated, determined by use of an ophthalmological measuring device, serve as input parameters for the calculation process; for another, the data of the (1 . . . n) IOLs that are possibilities for implantation serve for this purpose. These IOLs typically vary by IOL type (including variation of their asphericity or toricity) and IOL refractive power.

A wide-spread method for determining the refraction of the patient after insertion of the IOL is represented by what are called IOL formulas. Along with measured parameters, the IOL formulas are based on additional correction factors, on the basis of their simplified model assumptions. Depending on the IOL formula used, for example according to Holladay, Hoffer, Binkhorst, Colenbrander, Shammas or SRK, the approaches are correspondingly different.

In order to adapt the result of the calculation to the optimal refraction values that occur in a real case, correction factors determined empirically by way of a patient ensemble are used. However, this adaptation only ensures that the average value of the refraction values agrees with the formula for the test ensemble. Statistical errors that necessarily occur can typically be taken into consideration by the physician only on the basis of his/her experience, in that he/she corrects the calculated target refraction accordingly.

In order to minimize systematic errors in the calculation and selection of an IOL to be implanted in an eye, different approaches are selected at present, in accordance with the state of the art.

An alternative but not yet very wide-spread method is ray tracing. Ray tracing, as the term indicates ("ray"=ray and "to trace"=to trace), should be understood to be a method for ray tracing.

It is known that we perceive objects in our surroundings only because they are irradiated by a light source and they reflect these light rays, part of which rays finally reach our eyes. The ray tracing method simulates this elementary natural phenomenon. If the optical system, i.e. the individual human eye, is known with all of its optical elements, then a "real" image that occurs on the retina can be calculated by means application of ray tracing. The method is therefore based on a detailed eye model, using the cornea topography of the eye.

It is true that in this method, no general correction factors are used, but certain assumptions are required as far as the effective (post-operative) lens position (ELP) is concerned. This method is suitable for eyes having the most varied biometric parameters, such as, for example: long, normal, short, post-LASIK, etc.

Using ray tracing, the IOL refractive value and the residual refraction are then calculated. In order to achieve a good correlation with the subjective visual acuity, i.e. a result comparable with the perception of the patient, different selection criteria or metrics can be used for the calculation. Although retinal image metrics have proven to be particularly suitable in this regard, other optical evaluation parameters or selection criteria known to a person skilled in the art can also be used.

While a comparison between the use of ray tracing methods and IOL formulas is undertaken by P.-R. Preussner et al. in [1], they deal with a calculation model for ray tracing in [2]. Based on the individual measured values and the estimated variables, an eye model is developed here. The imaging quality at the retina/fovea is determined as an evaluation value here.

Because of the complexity of the entire process of cataract surgery, use of the method of ray tracing alone for calculating the IOL is not sufficient to guarantee that the result of the calculation of the post-operative refraction is better than with the formula approaches.

The most important prerequisite for successful ray tracing is precise and reproducible collection and analysis of the pre-operative measured data. Data collection determines the limits as to how complex an eye model that serves as the basis for the calculation can be. Prediction of the effective or real post-operative position and location of the implanted IOL is a further factor that is just as decisive as the surgical procedure and the subsequent healing process itself.

Numerous measuring methods for precise and reproducible collection and analysis of the pre-operative measured data are known from the state of the art; these vary with regard to the parameter to be measured, because no universal measuring method exists.

For example, numerous measuring techniques based on reflection, such as keratometers, Placido and other topographs, Scheimpflug cameras and slit lamps exist for measuring the cornea curvature, particularly its anterior surface and thickness, as do measuring techniques that are based on optical coherence tomography. Each of these technologies has advantages and disadvantages.

For example, it is true that very robust and reproducible measurements, but only a very simple model of the cornea can be implemented using distance-independent, telecentric keratometers. In contrast to this, topographs with a Placido disk offer detailed information about the cornea surface, but the reproducibility of the measured values is not comparable with telecentric keratometry.

Because Scheimpflug-based and OCT-based devices do not measure the entire region of interest at the same time, they are therefore affected by movement artifacts of the eye. However, they have the advantage, as compared with keratometers and Placido-based topographs, of allowing measurements of the posterior cornea surface, as well.

Something similar holds true for the determination of other biometric parameters of the eye required for calculating and selecting an IOL, such as anterior chamber depth, lens thickness, and eye length. The eye models known in the state of the art, such as those of Gauss, Liu-Brennan, and others, for example, are generally based on schematic models. It is true that in this regard, specific parameters can be replaced with individual measured data of patients, but theoretical definitions, reference points or axes generally remain fixed as the basis of schematic models.

In the end result, reference points or axes of the schematic eye models frequently do not coincide with the reference points or axes of the biometric data from the measuring devices.

As has already been mentioned, prediction of the post-operative position and location of the implanted IOL is also a decisive factor. Formula approaches for statistical optimization, for example, are known for prediction. In this regard, all the variables that influence the refractive results post-operatively are taken into consideration for determining the effective lens position. Such formula approaches are only possible with reference to the average population.

A method for calculating an intraocular lens to be implanted, in which method the results of numerous cataract operations are used in order to automatically optimize the calculation of intraocular lenses to be implanted in the future, is described in WO 2013/037946 A1. For this purpose, a post-operative determination of biometric data as well as of the objective, wave-front-based residual refraction takes place. The measured values determined pre-operatively and post-operatively are used for optimization of the surgically induced astigmatism and of the anatomical, post-operative lens position, and are included in the calculation of future IOLs to be implanted. In order for the proposed method to produce a noticeable effect, a correspondingly great number of data of post-operative measurements is required.

DE 10 2011 106 714 A1 describes a method for optimized prediction of the post-operative, anatomical position of an implanted intraocular lens, in that the post-operative lens position is predicted on the basis of known measured values, such as the cornea thickness, the anterior chamber depth, the eye length, as well as the distances of the capsular sac equator or of the lens haptic from the anterior lens surface. In this regard, the location of the intraocular lens to be implanted is included in the calculation, along with the anatomical, post-operative position of the lens, and additional parameters of the pseudophakic eye, which parameters have not yet been taken into consideration, are used for this purpose. The method is based on the use of suitable calculation methods, biometric formulas or ray tracing.

Other methods can provide a more direct prediction in that the IOL position is estimated on the basis of the individual biometric data. See U.S. Pat. No. 5,968,095 A in this regard.

In the solution described in DE 10 2011 103 224 A1, a precise prediction of the post-operative location of the IOL is supposed to be achieved in that along with an IOL, operation parameters within the scope of the IOL implantation are also selected. In this regard, corresponding starting parameters are determined from predetermined, estimated or measured input parameters, in that at least two input parameters are varied with one another, at least one input parameter of which is present as a distribution function. The resulting distribution function(s) is/are optimized using corresponding target defaults and used as a decision aid.

However, on the basis of the limited complexity of eye models and of the general lack of information concerning design characteristics of IOLs, an even more precise prediction of the post-operative position and location of an implanted IOL is not possible.

For this purpose, additional statistical correction factors both with regard to the IOL design and with regard to the average population would necessarily be required.

A problem in the selection of the IOL to be implanted can be seen in that the selection takes place merely using the data calculated from the optical parameters, and the subjective aspect of seeing, i.e. the subjective vision performance is not taken into consideration.

In this regard, the complete optical and psycho-physical experiences with regard to the vision process of a patient should be understood to be the subjective vision performance, in which the light that strikes the retina by after transmission by the optical components of the eye is detected by the photoreceptors, and signal from the photoreceptors are processed, and transmitted to the visual cortex in the brain, where visual perception actually takes place.

A difficulty in cataract surgery now exists in that the subjective vision performance of a patient can only be measured after the operation, when it is already too late for corrections.

For this reason, subjective experiences of the patients relating to post-operative refraction must be statistically collected, in order to be able to use these in the selection of the IOL to be implanted.

Since the measurement principles known according to the state of the art are only suitable for determining the optical parameters of an eye, estimation of the subjective visual performance is very limited. A first step for taking into consideration the subjective visual performance can be seen in calculation of the retinal image field metrics, in which the contrast and the phase transfer function of an object are calculated by means of the optical components of the eye in the image plane of the retina, based on an individual optical aberrations. In addition, some psycho-physical aspects of human vision can be taken into consideration by means of calculating the contrast transfer function.

Calculation of the retinal image metrics of a higher and/or lower order are equally practical not only for spherical and aspheric IOL designs but also for toric and multi-focal IOL designs, in order to facilitate the determination of the target refraction by means of simulation of the complex interactions between IOL and eye.

In the following, individual solutions will be discussed, with which the process of measuring, calculating, and selecting the IOL to be implanted is supposed to be improved.

In DE 10 2011 103 223 A1, a method for pre-operative selection of an intraocular lens to be implanted in an eye is described. IOLs that appear suitable are selected on the basis of an individual eye model, using their optical parameters, and the residual refraction is calculated by means of ray tracing for the IOLs that appear suitable. The decision regarding selection of an IOL is facilitated for the physician in that it is possible to compare IOLs that appear suitable with one another, and to take special requirements, criteria or parameters into consideration when making the selection.

The patent application DE 10 2012 019 473.0, not yet published, proposes a method for reliable determination of the axis length of an eye, in which method the axis length of an eye is determined by means of optical coherence tomography (OCT). In this regard, the alignment of the measuring device relative to the eye is monitored for all one-dimensional and two-dimensional scans, in order to be able to guarantee a reliable determination of the axis length of the eye. For this purpose, the retinal tissue structure detected from the B scans is segmented using one or different criteria, the fovea is detected, and its lateral distance from the optical axis of the measuring device is determined.

The patent application DE 10 2012 019 474.9, also not yet published, describes an apparatus for reliable determination of biometric measurement variables of the entire eye, as they are required for calculating IOLs by formulas or ray tracing. For this purpose, the surfaces of the entire eye that are optically relevant for the visual capacity of the eye are determined in terms of their location and their profile in the eye. The measurement arrangement used for this purpose consists of a multi-point keratometer and an OCT arrangement, wherein telemetric illumination and telecentric detection take place by means of the multi-point keratometer, and the OCT arrangement is designed as a laterally scanning swept-source system.

A method for imaging systems with which eye movements are monitored and compensated is described in U.S. Pat. No. 7,452,077 B2. In this regard, the likeness of an image projected into the eye is used to detect the current eye position. Tracking of eye movements allows precise registration of image data for the scan sites and thereby improved imaging. In order to be able to register a recorded pachymetry card precisely, the cornea vertex (vertex) must be recorded. The relationship between the highest point of the cornea arch in every B scan and the vertex is used to adjust the image, to indicate decentering correctly, and to correct errors in the pachymetry card.

In WO 2012/062453 A1, a method for model-based determination of the biometrics of eyes is described. The method for determining multiple lengths and other variables using localized boundary surfaces is based on optical coherence tomography. For this purpose, different scans are implemented with different scan patterns and focus settings, in order to adapt a parametric eye model accordingly. The biometric measured values can be derived from this adapted eye model. It is absolutely necessary, in this regard, that the scans that are implemented contain at least two of the boundary surfaces of the eye, in each instance.

All of the known solutions have the disadvantage that although they improve individual aspects of the process of measuring, calculating, and selecting the IOL to be implanted, considered in and of themselves they cannot, however, produce any qualitative jump in the determination of the target refraction and the selection of the intraocular lens to be implanted in an eye.

WO 2010/035139 A2 describes a solution for configuring and implanting a customized intraocular lens, in which the eye of a patient is analyzed and its biometric data are recorded. The system also comprises a modeling module and an optimization module, in order to produce an optimized IOL model, as well as a module for producing the customized IOL based on the IOL model. The goal of the solution proposed here can be seen in creating the IOL that best meets the requirements of the patient, using the biometric measured values and special specifications of the surgeon. This has the disadvantage that the psycho-physical experiences with regard to the vision process of a patient, in particular, are not taken into consideration.

LITERATURE

[1] Preussner, P.-R. et al., "Intraocular lens calculation accuracy limits in normal eyes," J CATARACT REFRACT SURG—VOL 34, May 2008,

[2] Preussner, P.-R. et al., "Ray tracing for intraocular lens calculation," J CATARACT REFRACT SURG—VOL 28, August 2002.

SUMMARY OF THE INVENTION

The present invention is based on the task of developing a solution with which the selection of an intraocular lens to be implanted in an eye is simplified, the disadvantages of the solutions known from the state of the art are eliminated, and the results of refractive procedures on the eye are optimized. In this regard, the solution to be developed should take into consideration all the aspects that have an influence on the selection of the IOL and, in particular, on the post-operative refraction result, if possible.

This task is accomplished with the method for optimizing the selection of the IOL to be implanted in an eye, in accordance with the method steps a) determining the required biometrical parameters of the eye, b) using said parameters for a corresponding eye model, c) calculating the data of an IOL to be implanted, by application of ray tracing, d) selecting an IOL to be implanted, on the basis of these data, and e) repeating the method steps c) and d) for further suitable IOLs, according to the invention, in that in order to optimize the method, in method step a), different measuring methods are optionally used as a function of the respective biometric parameter to be determined; in method step b), a corresponding patient-specific eye model is determined using the parameters; and in method step d), when selecting the IOL to be implanted, additional retinal image metrics are taken into consideration along with the data determined.

With the proposed solution, a method is made available, with which optimized selection of the intraocular lens to be implanted in an eye is possible. Because the method is suitable not only for spherical and aspheric IOLs but also for toric and multi-focal IOLs, nothing stands in the way of broad use.

DETAILED DESCRIPTION

Figure 1:
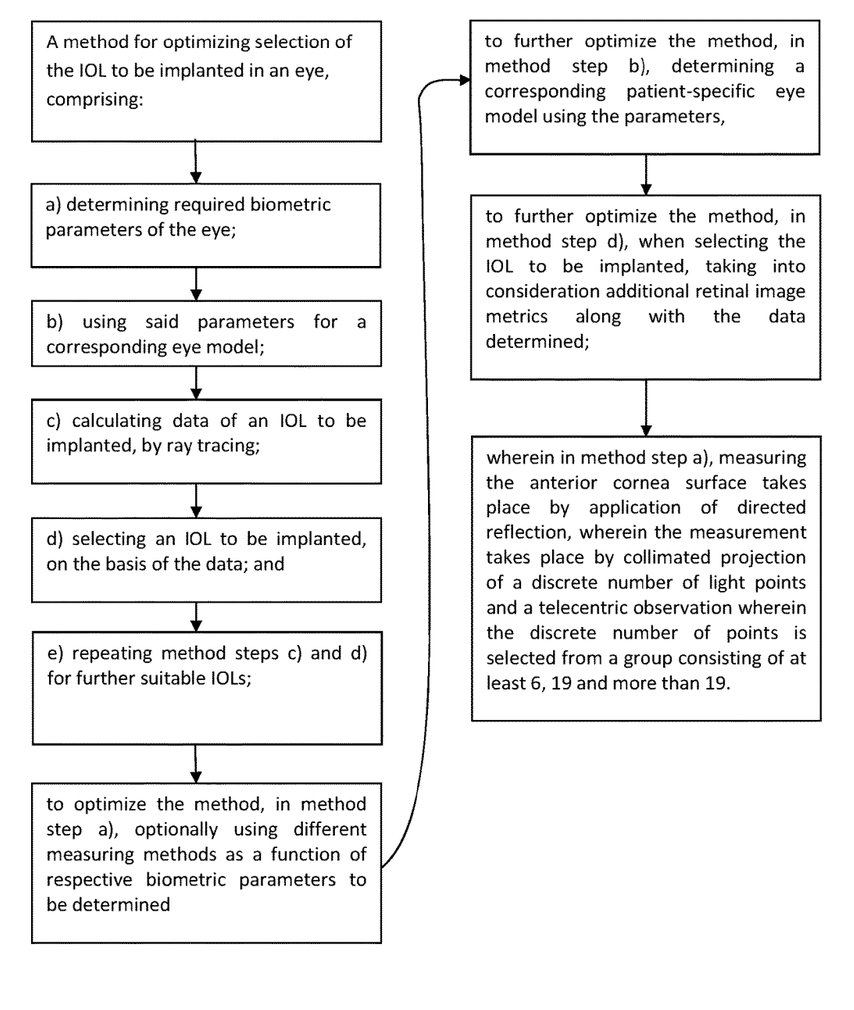
The FIGURE is a flowchart depicting a method according to an example embodiment of the invention.

The invention will be described in greater detail below, using example embodiments and with reference to the FIG.

In the proposed method, optimized selection of the IOL to be implanted in an eye takes place in accordance with the method steps a) determining the required biometrical parameters of the eye, b) using said parameters for a corresponding eye model, c) calculating the data of an IOL to be implanted, by application of ray tracing, d) selecting an IOL to be implanted, on the basis of these data, and e) repeating the method steps c) and d) for further suitable IOLs.

In order to optimize the method, according to the invention in method step a), different measuring methods are optionally used as a function of the respective biometric parameter to be determined, in method step b), a corresponding patient-specific eye model is determined using the parameters, and in method step d), when selecting the IOL to be implanted, additional retinal image metrics are taken into consideration along with the data determined.

Method Step a):

As has already been explained, in method step a), different measuring methods are used as a function of the respective biometric parameter to be determined.

For example, the anterior cornea surface is measured by directed reflection, by collimated projection of a discrete number of light points. In this regard, observation takes place in telecentric manner. This has the advantage that the measurement can take place in a "fuzziness range" of +/−1 mm, independent of the distance and the lateral alignment of the measuring device. The arrangement used for collimated projection of a discrete number of light points, by directed reflection, can be not only a keratometer but also a Fresnel lens or the like, in this regard.

For the measurement of the anterior cornea surface by means of directed reflection, at least 6 and for example 19 or more light points are projected onto the cornea, wherein it can be advantageous that a central light point is present, which is projected onto the cornea parallel to the Z axis.

According to example embodiments, the 6-point projection takes place without a central light spot, and the 19-point projection takes place with one. In this regard, the reconstruction of the topography of the cornea becomes simpler and more precise, the more light points are projected and afterwards recorded.

Furthermore, it is advantageous if the measured values from multiple measurements are used for determining the anterior cornea surface, in that these values are aggregated by application of statistical methods. To avoid incorrect measurements, it is practical if the measurements of a set take place within a blink interval or multiple blink intervals. A set for example, consists of 15 measurements that are implemented within a measuring time of less than 2 seconds.

In this method step, particularly when measuring the anterior cornea surface, it is additionally advantageous if the measurements are subjected to a quality evaluation. In this regard, the following criteria can be applied:

shape and intensity of the light points, temporal stability of the positions of the light points relative to one another, temporal stability of the positions of the light points relative to the eye, consistency of the individual measurements, and presence of imperfections.

It is important to the invention, in this method step, that the reconstruction of the anterior cornea surface takes place as a free-form surface, for example by the use of Zernike polynomials.

In accordance with an example embodiment, 19 light points, for example, are used for this purpose, in order to achieve a good compromise between good reproducibility and a great number of model details. The reconstruction takes place with a basic sphere and between 6 and 18 Zernike coefficients.

In the projection of a plurality of light points, correspondingly more Zernike coefficients are used.

Of course, the method proposed is not restricted to the use of Zernike coefficients. Instead, other forms of basic functions can also be used.

In contrast to the anterior cornea surface, which was measured by application of directed reflection, using collimated projection of a discrete number of light points, the cornea thickness is measured on the basis of a short-coherent, interference-optical method, parallel to the z axis, wherein measurements take place in the form of scans in different directions.

The cornea thickness is defined as the distance between the epithelial layer and endothelial layer of the cornea.

For example, measuring the cornea thickness takes place on an OCT basis as B scans along n meridians, which are for example, repeated m times.

An advantageous embodiment provides that n=6 OCT-based B scans are implemented at m=3 repetitions, for example, along the meridians at 0°, 30°, 60°, 90°, 120°, and 150°.

Measuring the corneal thickness takes place within a central zone about the z axis, having a diameter of approximately 2 mm, according to another embodiment 4 mm, and according to a further embodiment at least 6 mm.

According to an example embodiment of the invention, for the determination of the cornea thickness, the posterior cornea surface is reconstructed from the B scans, taking into consideration the anterior cornea surface that has already been determined, wherein known methods of image processing are used.

Reconstruction of the posterior cornea surface has the advantage that the thickness of the cornea can thereby be determined at any desired location, as a distance from the anterior cornea surface. Lateral eye movements that occur while measuring the cornea thickness can be balanced out with known methods here, as well.

Just like measuring the cornea thickness, measuring the anterior chamber depth, lens thickness, and eye length also takes place on the basis of a short-coherent, interference-optical method. For example, the scans for measuring the cornea thickness are used, in that the corresponding boundary surfaces are detected using known methods of image processing.

In this regard, the length measurements take place along an axis v that runs through the vertex and parallel to the vertex normal line. In this regard, the distances are defined as follows:

anterior chamber depth: distance between anterior cornea surface and anterior lens surface, lens thickness: distance between anterior and posterior surface of the lens, and eye length: distance between anterior cornea surface and the retinal pigment epithelium (abbreviated: RPE).

According to the invention, not only the thickness of the lens but also its decentering and/or tilting is determined. According to an example embodiment, this takes place in two directions, for example horizontally and vertically.

To determine the eye length, detection of the fovea is carried out, for example by segmentation of the retinal tissue structure, in order to enable alignment of the optical axis of the measuring device with the vision axis of the eye.

Furthermore, it can be helpful to determine additional parameters, along with distances that are absolutely necessary for the selection of an IOL to be implanted in an eye, such as, for example, diameter of capsular sac and capsulorhexis, center point of the pupil region, as well as haptic diameter and haptic type.

Listed in greater detail, this can be, for example with reference to the natural eye lens:

the radii of curvature of the anterior and/or posterior side of the lens, its horizontal and/or vertical decentering, or also its tilting.

Aside from the diameter and the center point of the pupil region, which characterizes possible decentering of the pupil, the following parameters can also be of interest:
- diameter of capsular sac and capsulorhexis,
- diameter and haptic type of the IOL to be used,
- the distance of the capsular sac equator from the anterior surface of the lens,
- the thickness of the IOL, or
- the distance of the lens haptic from the anterior surface of the IOL.

In this regard, the term "capsulorhexis" is understood to mean opening up the anterior surface of the capsular sac in disk shape. In this process, the capsular sac is perforated and opened up using a tearing maneuver.

The "holders" used to fix the intraocular lens in place in the capsular sac are referred to as "haptics." The haptic is disposed peripherally around the actual optical lens and can be structured in different forms, such as brackets, plates or loops.

Using these additional data, it can be determined before implantation, for example, whether the selected IOL actually fits into the capsular sac, which can also be decentered relative to the cornea vertex, on the basis of its geometry. Furthermore, these data facilitate a prediction not only of the position of the IOL, but rather also of its location, i.e. its decentering in the x, y, and z direction, and vertical and/or horizontal inclination relative to the peak of the cornea vertex and its normal line.

As was described with regard to previous measurements, it is practical here, as well, to subject the values measured for anterior chamber depth, lens thickness, and eye length to a plausibility check.

Method Step b):

As has already been explained, in method step b), a corresponding, patient-specific eye model is determined using the parameters that were determined.

According to the invention, the patient-specific eye model comprises not only boundary surfaces in the form of freeform surfaces with all degrees of freedom, but rather for all the boundary surfaces present behind the anterior cornea surface, their tilting with reference to the x-y plane of the cornea vertex as well as their decentering with reference to the cornea vertex are taken into consideration.

In this regard, the clearly detectable cornea vertex as well as its vertex normal line serves as a reference point or reference center (coordinate origin).

It is particularly advantageous, in this regard, that in the patient-specific eye model, the individual location and position of the eye lens is taken into consideration as the probable location and position of the IOL to be implanted, with possible decentering and/or tilting.

For correct ray tracing, the patient-specific eye model should also contain the location of the pupil. Decentering is also taken into consideration with regard to the pupil opening. Because possible tilting influences the opening surface that has been detected in any case, a separate determination is not necessary.

Determination of the opening surface of the pupil is also significant for ray tracing, because this surface is circular only in rare cases. As has already been described, the position of the pupil center is clearly defined with reference to the cornea vertex.

Because the shape of the retina in the patient-specific eye model is furthermore decisive for correct ray tracing, this shape is preferably defined as a sphere sector, with a radius of curvature corresponding to the vitreous body depth.

With regard to the indices of refraction of the media between the boundary surfaces, reference is made to indices for schematic model eyes known from the literature. In this regard, the index of refraction of air is set to air=1, and the others are put into relation with this as relative indices of refraction. The indices of refraction are dependent on the wavelength of the light used, and are as follows, for example, for yellow light having a wavelength of 587 nm:
- air: 1.0000
- cornea: 1.376
- anterior chamber: 1.336
- natural vitreous body: 1.336
- treated vitreous body: as per manufacturer information, and
- IOL: as per manufacturer information.

The patient-specific eye model comprises the complete geometrical description of all elements required for simulation, as well as the indices of refraction of the materials that pass through the simulation. The sequence of elements as well as the indices of refraction of all the media, aside from that of the IOL, are defined in fixed manner and are set with a special initialization routine. This initialization is a prerequisite for all subsequent data operations on the eye model.

The geometric parameters of the elements are set by means of special routines for the patient eye to be simulated, in each instance. Within these routines, the data values are checked for reliability. Setting patient data is only permissible if an initialized eye model is available. The sequence in which the patient data are set is arbitrary. Data that have been set are not allowed to be overwritten by setting them again. Special routines for changing values that have already been set are offered only for some patient data.

A complete eye model is present when the optical imaging has been defined. Setting the values required for this can take place in any desired sequence. While they are set, the values are checked for reliability. Setting of the imaging data is only permissible if an initialized eye model is present.

A complete eye model is present if the following data have been set:

Initialization Data (Sequence of the Boundary Surfaces)
object-air-plane of the cornea vertex-air-anterior cornea surface-cornea medium-posterior cornea surface-anterior chamber medium-pupil plane-anterior chamber medium-anterior IOL surface-haptic plane-posterior IOL surface-vitreous body medium-retina.

The indices of refraction of cornea medium, anterior chamber medium, and vitreous body medium are described by separate coefficients of the Sellmeier formula, pre-set in the program.

Patient Data (Shapes/Decentering/Tilting of the Boundary Surfaces)

| | |
|---|---|
| shape of the anterior cornea surface | description either by means of Zernike coefficients or with different conical sections in the x-z or y-z plane |
| center thickness of the cornea | |
| shape of the posterior cornea surface | description relative to the shape of the anterior cornea surface by means of a scaling factor, or directly from the OCT measurement |
| location of the pupil plane | distance from the cornea vertex, offset in x and y direction |

-continued

| location of the haptic plane | distance from the cornea vertex, offset in x and y direction, tilting about x and y axis |
| location and shape of the retina | distance from cornea vertex, radius of curvature |

The location of the pupil plane and the location of the haptic plane are allowed to be changed during the further course of events. All other patient data cannot be changed without new initialization of the eye model.

IOL Data

| spherical refractive power | for all IOL types |
| cylindrical refractive power | for toric IOLs |
| angle of rotation in the haptic plane | for toric IOLs |
| data model | for multi-focal IOLs |

Imaging Data

| object | type of object location, in the case of a finite object: distance from the cornea vertex |
| pupil | diameter |
| image | location of the image plane in the retina |

Before every calculation of the eye model, a check takes place as to whether all the required data have been set on the eye model. Failed checks when setting data or when reviewing the entire eye model result in a specific error code.

The selection of an IOL from the currently stored catalog is only permissible if a complete and initialized eye model is present.

Method Step c):

As has already been explained, in step c), calculation of the data of an IOL to be implanted takes place by application of ray tracing.

According to the invention, light rays are used for ray tracing for calculating the data of an IOL to be implanted, which rays, proceeding from a virtual object, are projected onto the eye, wherein the distance of the virtual object can vary.

This has the result that the light rays of the ray bundle run parallel and divergent at a slight distance in the case of a great distance (coming from the "infinite").

Preferably, the region of the light rays used as a ray bundle is variable as a function of the actual pupil surface or cornea surface. For this reason, the diameter of the bundle of light rays should cover at least the entire region of the entry pupil. In this regard, however, it must be taken into consideration that extrapolation of the cornea surface, which contains many degrees of freedom, based on few measurement points, becomes critical.

According to a first embodiment, the light rays used for ray tracing are monochromatic, wherein the wavelength can vary as a function of the default values of the respective patient. However, a color in the vicinity of the sensitivity maximum of the eye, particularly the color green/yellow, is preferred according to an example embodiment of the invention.

According to a second embodiment, the light rays used for ray tracing are polychromatic. This allows a possibly better selection, because now colors to which the eye is less sensitive can also be taken into consideration. This furthermore has the advantage that it can be taken into consideration in calculating the IOL to be implanted what preferences or habits the patient has. By changing the wavelength distribution (weighting), the selection can be optimized for special lighting situations, such as, for example, natural light, incandescent lamp light, fluorescent lamp light or the like.

If the IOL to be implanted is supposed to be optimized for improved twilight vision, it must be taken into consideration that on the one hand, twilight vision is characterized by a large pupil opening, and, on the other hand, that the rods situated in the retina of the eye are predominantly used. Because these prefer different wavelengths as compared with the cones, it is therefore appropriate to use either adapted monochromatic or correspondingly weighted polychromatic light rays for ray tracing.

Just like for calculation of the data of the IOL to be implanted, light rays that are projected onto the eye proceeding from a virtual object are also used for calculation for simulation of the visual performance of the eye, which rays are projected onto the eye, proceeding from a virtual object, wherein the distance of the virtual object can vary.

Method Step d):

As has already been explained, in method step d), when selecting the IOL to be implanted, additional retinal image metrics are taken into consideration along with the data determined.

According to the invention, different metrics, for example retinal image metrics closely correlated with subjective visual perception, are used for selecting the IOL to be implanted.

As has already been explained, a problem can be seen in the selection of an IOL to be implanted, in that the selection takes place merely on the basis of the data calculated from the optical parameters, and that the subjective visual performance, i.e. the psycho-physical experiences with regard to the vision process of a patient is/are not taken into consideration.

The retinal image metrics are suitable for simulating the relationships between the optical quality (on the retina) and the visual performance (in the vision cortex) and for selecting the IOL for an individual eye that best corresponds to the desired post-operative vision performance.

According to an example embodiment, the visual Strehl ratio of the modulation transfer function of the retinal image metrics is taken into consideration in connection with the contrast transfer function.

In accordance with a further example embodiment, a visual performance comparison with regard to the simulated visual acuity or the simulated depth of focus, based on retinal image metrics, is used for evaluating the quality of the IOL in the individual eye model.

According to example embodiments of the invention, the selection of the IOL to be implanted takes place on the basis of the determined data from a catalog, in such a manner that all or part of the possible IOLs are selected, introduced into the patient-specific eye model, calculated by means of ray tracing, and the optimal IOL is selected on the basis of the metrics value. A catalog is understood to be a database in which IOLs are stored with their optical parameters or type properties. In practical manner, the data should be checked for reliability before selecting an IOL. For this purpose, a special routine can be called up, which checks all the required data of the catalog for existence and consistency.

The following parameters or type properties are important for use in the eye model:
surface shape: spherical, aspheric or toric,
type of design: refractive or diffractive,
number of foci: monofocal, bifocal or multifocal, per focus: energy proportion in focus,
difference of refractive power relative to the first focus,
diffractive surfaces: none, anterior, posterior or both,
dispersion function: none, Schott or Sellmeier,
in case of dispersion: coefficients of the dispersion formula,
in case of no dispersion: wavelengths with related indices of refraction,
delivery range of the spherical and cylindrical refractive powers,
number of spherical refractive powers that can be calculated, and
number of cylindrical refractive powers that can be calculated.

This listing is merely an example and is by no means conclusive.

Preferably, the geometric description of the IOL is stored for every refractive power. The amount of the geometry data is dependent on the surface shape and on the type of design. In the case of diffractive surfaces, the work can be done either with the actual geometry data or with a refractive equivalent. For the refractive equivalent, the surface shape is described with the same parameters as in the case of the refractive IOLs.

The following information can be stored, for example, as geometry data dependent on the surface shape and the type of design:
spherical refractive power,
cylindrical refractive power,
center thickness,
diameter,
radius of curvature,
conical constant,
development constants,
distance of the anterior surface from the haptic plane, etc.

The selection is made by indicating the spherical refractive power, and, in the case of toric IOLs, additionally by indicating the cylindrical refractive power. In order for this to be possible, precisely one IOL catalog with all the necessary data must be known.

According to example embodiments of the invention, the quality demands within the search algorithms are varied in steps, so that the search is refined with every step. For this purpose, the extreme of the metrics for possible IOLs is determined by the search algorithms, by a targeted change in the values of the available degrees of freedom. In the search algorithm for toric IOLs, special attention is paid to the sequence in which the available degrees of freedom are varied.

According to an example embodiment, for the selection of an IOL with rotation symmetry, the search algorithm selects the IOL that corresponds to the mean value of the IOLs previously determined for two different meridians. Preferably, the two meridians lie perpendicular to one another.

In a further example embodiment, during the search, it is checked in the search algorithm, by means of targeted overdrawing, whether an extreme that is found has only a local character.

In accordance with another example embodiment, not only the optimal IOL but rather a matrix of best suitable IOLs, which matrix contains images, the image quality of which corresponds to the vision determined, is made available to the user for selection of the IOL to be implanted. The selection then takes place after imaging with the best subjective impression, and this can lead to the result that the calculated optimal IOL is not selected.

The search for the best IOL for a patient eye fundamentally takes place for precisely one predetermined imaging task. Different metrics are available for evaluating the imaging quality. One of these metrics must be selected for the search. The currently uploaded IOL catalog is used as the search space. In the case of multifocal IOLs with diffractive surfaces, the search takes place with the refractive equivalent of the surface description.

In the case of IOLs with rotation symmetry, the spherical refractive power is the only degree of freedom for the search. In the case of toric IOLs, the cylindrical refractive power and the rotation of the IOL in the haptic plane are added as further degrees of freedom. In this regard, the rotation is determined with a precision of 1°.

An IOL of the current catalog must be selected as the starting point of the search. In the case of toric IOLs, the starting angle of rotation must also be predetermined. Therefore a complete eye model for the search is available once the imaging task has been established.

The search takes place according to the method described above. Each of the IOLs selected in this manner is introduced into the eye model, and the metrics for this eye are calculated. The result of the search is the IOL with the best metrics at a well-defined angle of rotation (the latter is only important for toric IOLs).

In the search, the extreme of the metrics is determined by means of targeted changing of the values of the available degrees of freedom. In this regard, it is checked during the search, by application of targeted overdrawing, whether an extreme that is found has only a local character. In order to ensure rapid convergence, the search is carried out in multiple steps. Because of the different number of degrees of freedom, different algorithms are used for IOLs with rotation symmetry and for toric IOLs, in a Smart Search.

In contrast to the method described here, in the case of a "brute-force algorithm," all the available degrees of freedom of the IOLs are set to every possible value within an established range, relative to the starting IOL, and this makes the search very time-consuming.

In the end result of the search, the best IOL and its metrics values are determined under the assumption of ideal implantation. However, since "implantation errors," i.e. incorrect positioning of the IOL can continue to occur in spite of a great number of such implantations, it is desirable to be able to take this into consideration in the selection.

The goal of what is called toleration now consists in determining the greatest possible worsening of the metrics value caused by implantation errors.

In this regard, it should be possible to take the following implantation errors into consideration:
distance of the haptic plane from the cornea vertex,
offset of the IOL in the x direction and y direction in the haptic plane, and
tilting of the haptic plane about the x axis and y axis.

For toric IOLs, it should also be possible to take the rotation of the IOL in the haptic plane into consideration.

In order to be able to carry out the toleration, a value must be predetermined and set on the complete eye model for every implantation error. In this regard, each implantation error individually must have both a positive value and also a negative value.

For each eye model that results in this way, the metrics are calculated and the worst value of all the metrics calculated in this manner is determined. Therefore the result of the toleration is the ratio of the worst metrics to the metrics of the ideally implanted eye in percent.

With the invention according to the invention, a method for optimizing the selection of the intraocular lens (IOL) to be implanted in an eye is made available, with which the results of refractive procedures on the eye are optimized.

With the present method, the selection of the intraocular lens to be implanted in an eye is significantly simplified and becomes safer.

The results of refractive procedures on the eye can be optimized by taking into consideration all the aspects that have an influence on the selection of the IOL and, in particular, have the post-operative refraction result to be achieved.

The aspects of the method that are important to the invention can be seen in that different measuring methods are optionally used as a function of the biometric parameter to be determined, in each instance, that a corresponding patient-specific eye model is determined on the basis of the parameters, that in calculating the IOL to be implanted, additional retinal image metrics are taken into consideration along with the data determined, and that a more rapid selection of the IOL to be implanted is possible by application of the algorithm described.

The invention claimed is:

1. A method for optimizing selection of the IOL to be implanted in an eye, comprising:
   a) determining required biometric parameters of the eye;
   b) using said parameters for a corresponding eye model;
   c) calculating data of an IOL to be implanted, by ray tracing;
   d) selecting an IOL to be implanted, on the basis of the data; and
   e) repeating method steps c) and d) for further suitable IOLs;
   further comprising, to optimize the method,
   in method step a), optionally using different measuring methods as a function of respective biometric parameters to be determined;
   in method step b), determining a corresponding patient-specific eye model using the parameters, and
   in method step d), when selecting the IOL to be implanted, taking into consideration additional retinal image metrics along with the data determined;
   wherein in method step a), measuring the anterior cornea surface takes place by application of directed reflection, wherein the measurement takes place by collimated projection of a discrete number of light points and a telecentric observation wherein the discrete number of points is selected from a group consisting of at least 6, 19 and more than 19.

2. The method according to claim 1, wherein the measurements are subjected to a quality evaluation, wherein one or more criteria selected from the following group are applied:
   shape and intensity of the light points,
   temporal stability of the positions of the light points relative to one another,
   temporal stability of the positions of the light points relative to the eye,
   consistency of the individual measurements, and
   presence of imperfections.

3. The method according to claim 1, further comprising reconstruction of the anterior cornea surface as a free-form surface.

4. The method according to claim 1, wherein the reconstruction further comprises the use of Zernike polynomials.

5. The method according to claim 1, wherein in method step a), measuring the cornea thickness takes place on a basis of a short-coherent, interference-optical method, parallel to the z axis, further wherein the measurement takes place on an OCT basis as a B scan along n meridians, wherein the measurement is repeated m times.

6. The method according to claim 5, further comprising implementing n=6 OCT-based B scans at m=3 repetitions.

7. The method according to claim 6, further comprising implementing the OCT-based B scans along the meridians at 0°, 30°, 60°, 90°, 120°, and 150°.

8. The method according to claim 5, wherein a zone for measuring the cornea thickness as a function of cornea radius and pupil opening has a diameter selected from a group consisting of 2 mm, 4 mm, and at least 6 mm.

9. The method according to claim 5, wherein for the determination of the cornea thickness, the posterior cornea surface is reconstructed from the B scans, taking into consideration the anterior cornea surface that has already been determined, wherein known methods of image processing are used.

10. The method according to claim 1, further comprising determining along with a thickness of the lens, decentering of the lens and/or tilting of the lens.

11. The method according to claim 1, further comprising determining anterior chamber depth, lens thickness, and eye length on a basis of a short-coherent, interference-optical method, and determining one or more additional parameters selected from a group consisting of a diameter of a lens capsule, a diameter of a capsulorhexis, a center point of the pupil region, haptic diameter and haptic type.

12. The method according to claim 11, further comprising for the determination of the eye length, detection of the fovea to enable alignment of the optical axis of the measuring device with the visual axis of the eye.

13. The method according to claim 12, further comprising detecting the fovea by segmentation of retinal tissue structure.

14. The method according to claim 1, wherein the patient-specific eye model contains boundary surfaces in the form of free-form surfaces with all degrees of freedom.

15. The method according to claim 14, further comprising, in the patient-specific eye model, taking into consideration for all boundary surfaces present behind the anterior corneal surface, tilting with regard to the x-y plane of the cornea vertex as well as decentration with regard to the cornea vertex.

16. The method according to claim 14, further comprising, in the patient-specific eye model, taking into account an individual location and position of the eye lens and the probable location and position of the IOL to be implanted, along with possible decentration and/or tilting.

17. The method according to claim 1, further comprising using light rays for ray tracing for calculating the data of the IOL to be implanted, which rays, proceeding from a virtual object, are projected onto the eye, wherein the distance of the virtual object can vary.

18. The method according to claim 17, wherein the light rays used for ray tracing are polychromatic or monochromatic, wherein wavelengths vary as a function of default values of a respective patient.

19. The method according to claim 17, wherein a region of the light rays used as a ray bundle is variable as a function of an actual pupil surface or cornea surface.

20. The method according to claim 17, further comprising using light rays in a calculation for simulation of visual performance of the eye, which rays are projected onto the eye, proceeding from a virtual object, wherein the distance of the virtual object can vary.

21. The method according to claim 1, further comprising using different metrics, closely related with subjective visual perception Including retinal image metrics, for selecting the IOL to be implanted.

22. The method according to claim 21, further comprising taking into consideration a visual Strehl ratio of a modulation transfer function of the retinal image metrics in connection with the contrast transfer function.

23. The method according to claim 21, further comprising using a visual performance comparison with regard to the simulated visual acuity, based on retinal image metrics, as a quality characteristic of the IOL in the individual eye model.

24. The method according to claim 21, further comprising using a visual performance comparison with regard to the simulated depth of focus, based on retinal image metrics, as a quality characteristic of the IOL in the individual eye model.

25. The method according to claim 21, wherein the selection takes place on the basis of the determined data from a catalog, such that all or part of possible IOLs are selected, introduced into the patient-specific eye model, calculated by ray tracing, and the optimal IOL is selected on the basis of the metrics value.

26. The method according to claim 25, further comprising making available not only an optimal IOL but rather a matrix of best suitable IOLs, based on simulation of the vision, to the user for selection of the IOL to be implanted.

27. The method according to claim 21, further comprising taking into consideration implantation errors in the selection of the IOL to be implanted, in that eye models are determined and metrics are calculated for possible implantation errors.

28. The method according to claim 21, wherein for the selection of an IOL with rotation symmetry, the search algorithm selects the IOL that corresponds to the mean value of the IOLs previously determined for two different meridians.

* * * * *

UNITED STATES PATENT AND TRADEMARK OFFICE
CERTIFICATE OF CORRECTION

PATENT NO. : 10,123,687 B2
APPLICATION NO. : 15/103299
DATED : November 13, 2018
INVENTOR(S) : Tobias Bühren et al.

It is certified that error appears in the above-identified patent and that said Letters Patent is hereby corrected as shown below:

In the Specification

Column 2, Line 21, delete "P.-R." and insert --P.R.--

Column 2, Line 22, after "et al.", insert --,--

Column 5, Line 24, delete "(vertex)"

Column 6, Line 19, after "step", insert --:--

Column 6, Lines 66-67, after "invention", insert --:--

Column 8, Line 49, delete "(abbreviated)"

Column 10, Line 11, after "1.0000", insert --,--

Column 10, Line 12, after "1.376", insert --,--

Column 10, Line 13, after "1.336", insert --,--

Column 10, Line 14, after "1.336", insert --,--

Column 13, Line 35, after "constants,", insert --and--

Signed and Sealed this
Fourteenth Day of January, 2020

Andrei Iancu
*Director of the United States Patent and Trademark Office*